United States Patent [19]
Araya et al.

[11] Patent Number: 5,559,333
[45] Date of Patent: Sep. 24, 1996

[54] APPARATUS OF NON-DISPERSIVE INFRARED ANALYZER

[75] Inventors: Katsuhiko Araya, Kyoto; Youzo Morita, Kameoka; Shingo Sumi, Moriyama; Hiroaki Matsuhisa, Muko, all of Japan

[73] Assignee: Shimadzu Corporation, Kyoto, Japan

[21] Appl. No.: 350,057

[22] Filed: Nov. 29, 1994

[30]       Foreign Application Priority Data

Nov. 29, 1993   [JP]   Japan ................................ 5-298579

[51] Int. Cl.⁶ .......................... G01N 21/35; G02B 5/20
[52] U.S. Cl. .................... 250/344; 250/343; 250/339.01; 250/338.1; 250/339.06; 250/341.1; 250/349; 250/339.12; 250/339.13
[58] Field of Search ........................... 250/344, 343, 250/338.1, 339.01, 339.06, 341.1, 349, 339.12, 339.13

[56]             References Cited

U.S. PATENT DOCUMENTS

| | | | |
|---|---|---|---|
| 2,951,939 | 9/1960 | Luft | 250/344 |
| 3,162,761 | 12/1964 | Luft | 250/344 |
| 3,860,344 | 1/1975 | Garfunkel | 250/339.13 |
| 3,904,880 | 9/1975 | Benz et al. | 250/339.13 |
| 4,084,906 | 4/1978 | Bibero | 250/343 |
| 5,036,198 | 7/1991 | Spaeth | 250/339.13 |

Primary Examiner—Constantine Hannaher
Assistant Examiner—Virgil Orlando Tyler
Attorney, Agent, or Firm—Nikaido, Marmelstein, Murray & Oram LLP

[57]             ABSTRACT

A non-dispersive infrared analyzer and method for analyzing a concentration in a gas utilizes an infrared light source and a cell configured to have a gas flow therethrough. The cell also has an infrared light passage through which a sample gas stream and an infrared light beam can travel. A sector has at least two filters for filtering infrared light, and is provided with the apparatus. The sector alternately inserts the at least two filters into the infrared beam. A detector detects wavelengths of the infrared light beam which corresponds to an absorption band of the gas to be measured, and a second wavelength which corresponds to an absorption band of the preselected reference gas. The detector receives the infrared light beam after the light beam has traveled through the sample cell. The detector generates an electrical signal based upon the detected infrared light, which is correlated with a position indicating apparatus to provide a normalized intensity ratio, which is used to calculate the concentration of the gas to be measured in the cell.

14 Claims, 7 Drawing Sheets

APPARATUS OF NON-DISPERSIVE INFRARED ANALYZER

BACKGROUND OF THE INVENTION

(1) Field of the Invention

The present invention relates to a non-dispersive infrared analyzer for detecting concentration of a preselected gas in a sample gas using an absorption band of infrared light which is characteristic of the preselected gas.

(2) Description of the Related Art

Non-dispersive infrared analyzers are now widely used in measuring gas concentration of various types of exhaust gases in order to monitor the exhausts for air pollution, for measuring gas concentration in industrial processes, etc. One such non-dispersive infrared analyzer, as an example, is described in U.S. Pat. No. 4,355,233 by Warnke et al.

Figure 5:
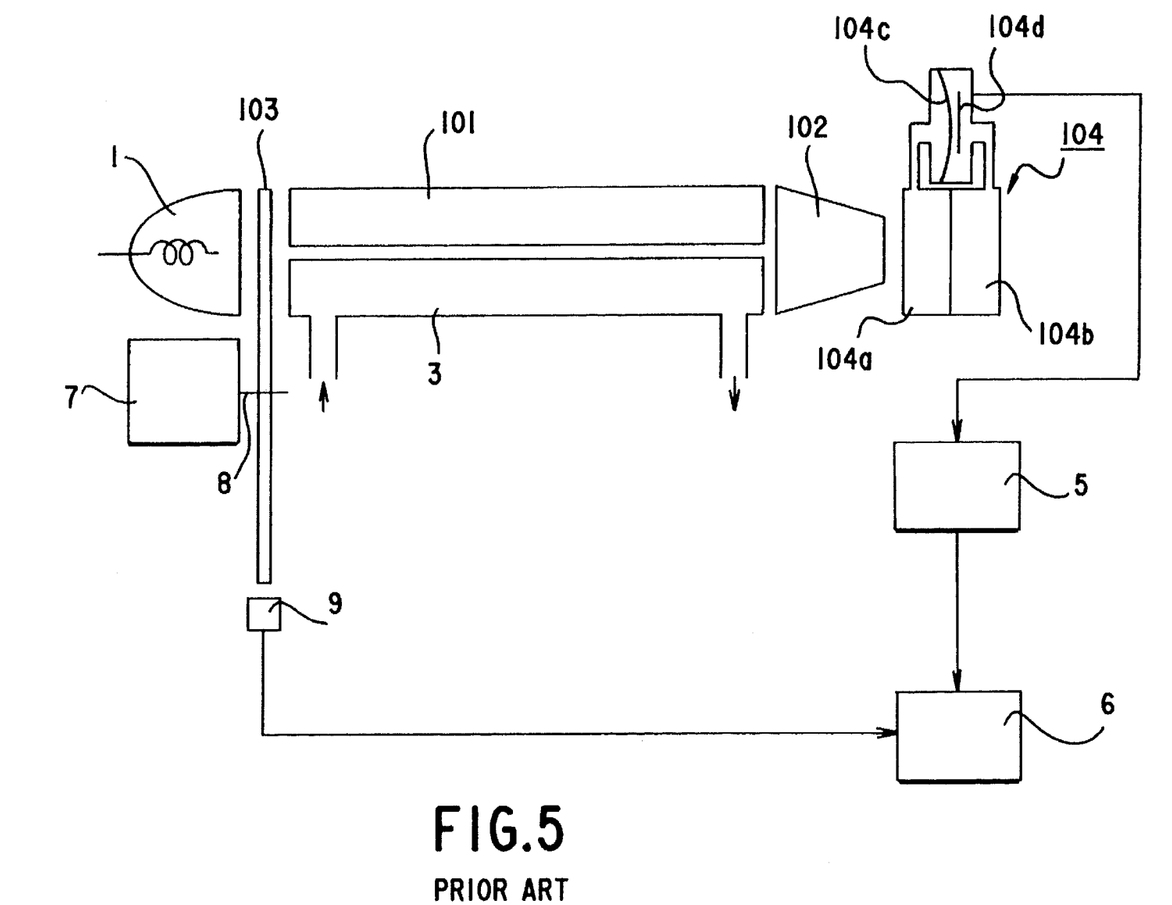
FIG. 5 illustrates a prior art dual beam non-dispersive infrared analyzer.
Figure 6:
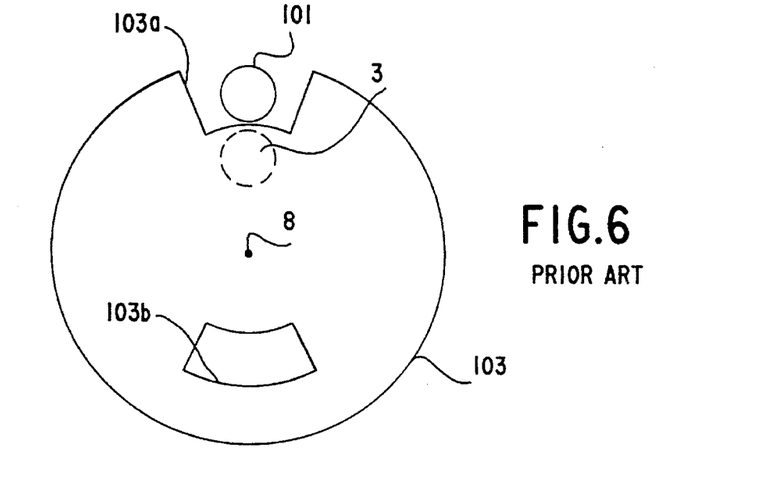
FIG. 6 depicts a prior art rotating chopper.

A prior art dual beam non-dispersive infrared analyzer is illustrated herein in FIG. 5. FIG. 6 depicts a rotating chopper thereof. In the FIG. 5, item 1 indicates an infrared source, item 3 is a cylindrical sample cell, item 5 is an amplifier, item 6 is an electric circuit, item 7 is a motor, item 8 is an axle connected to the motor, item 9 is a position sensor, item 101 is a cylindrical reference cell, item 102 is a light collector, item 103 is a rotating chopper having a disc shape, and item 104 is a pneumatic detector. Item 103a of FIG. 6 is a first aperture located at an outer track of the rotating chopper, and 103b is a second aperture located at an inner track of the rotating chopper.

The cylindrical walls of sample cell 3 and reference cell 101 are typically formed of aluminum. Both ends of the cylindrical cells 3 and 101 are equipped with cell windows through which an infrared light beam passes. The cell windows are made of plate which is transparent to infrared light, such as calcium fluoride, $CaF_2$.

In practice, the infrared source 1 emits a wide spectrum of infrared radiation. The rotating chopper 103 is operated to interrupt the infrared light by periodical rotation, for example, one rotation per one second (1 Hz). The infrared radiation travels to the reference cell 101 through the first aperture 103a and to the sample cell 3 through the second aperture 103b, respectively. In the sample cell 3, a specimen gas which includes the gas to be measured, flows through. The reference cell 101 is an airtight cell and is filled with a gas which does not absorb infrared energy, such as $N_2$ gas. The beam, having traveled through the sample cell 3 or the reference cell 101, reaches detector 104 which has selective sensitivity of the infrared radiation band set to correspond with the absorption wavelength of a gas to be measured.

Detector 104 can be a pneumatic detector, which is a one type of such detector. Detector chamber 104a and 104b are generally filled with the same kind of gas as that to be measured, and are separated by a diaphragm 104c. Diaphragm 104c is a very thin sheet of a conductive material such as titanium foil which serves as a variable plate of a capacitor. Disposed next to diaphragm 104c is an electrode 104d which serves as a fixed plate of the capacitor. Infrared energy within the absorption band, characteristic of the gas to be measured, which has not been absorbed by the component gas in sample cell 3, will be absorbed by the same gas in the chamber 104a. The gas in the chamber 104a will become heated to a greater extent than that in the chamber 104b. The unequal heating in the chambers 104a and 104b will produce a pressure difference, causing deflection of diaphragm 104c which, in turn, will vary the capacitance established between electrode 104d and diaphragm 104c.

Detector 104 generates an electric signal, which is then amplified by amplifier 5. The signal is fed to electrical circuit 6.

Rotating chopper 103 is connected to the motor by the axle 8, and rotates periodically. The infrared radiation emitted by the infrared source is exposed to the reference cell 103 and the sample cell 3 alternatively and periodically in a time-sharing manner through the first aperture 103a and the second aperture 103b of rotating chopper 103. Also, position sensor 9 which is placed near outer track of the chopper disk, senses the first aperture, and feeds the position signal to the electrical circuit 6. The electrical circuit determines whether the detector signal belongs to the sample signal generated by the beam traveled through the sample cell 3 or the reference signal generated by the beam traveled through the reference cell 101.

In order to eliminate an effect caused by the fluctuation of the intensity of emitted light and/or the fluctuation of the sensitivity of detector 104, caused by variables such as temperature, the sample signal is normalized using the reference signal. The sample signal is divided by the reference signal, and the normalized intensity ratio is obtained. Because the intensity ratio is proportional to the concentration of the gas to be measured in the sample cell, the electrical circuit calculates the concentration of the gas to be measured.

As mentioned above, a prior art dual beam non-dispersive infrared analyzer employs dual cells. Very often, the two cells will have different permeability of infrared light due to, for example, stains on cell window and/or on inner wall of the cell caused by constituent of sample gas. Also, the light collector may not be completely symmetrical for the two beams, which can introduce inconsistencies in the reading of the beams. Because the normalization of the sample signal by the reference signal is based on the hypothesis that the two beams passing through the cells are of equal character concerning infrared light, these differences or inconsistencies can render the output concentration result inaccurate. Thus, balance adjustment of the two beam passes is necessary.

Further, the structure of the infrared analyzer is complicated due to the dual beam structure. Moreover, since the infrared radiation goes through the relatively small aperture to travel to the cells in a time-sharing manner with the rotation of the chopper, the utilized portion of the emitted infrared radiation for the measurement is less than one fourth (¼) of the emitted radiation by infrared source. In order to overcome this drawback, or minimize the effect thereof, cell inner walls of some of prior art apparatuses are plated with gold.

It is therefore an object of the present invention to provide a simple single beam, non-dispersive infrared analyzer having high accuracy.

It is another object of the present invention to provide compensation means to rectify a fluctuation of the overall sensitivity of the non-dispersive infrared analyzer.

It is further object of the present invention to provide an inexpensive non-dispersive infrared analyzer for measuring gas concentration in a sample gas stream.

It is further object of the present invention to provide an non-dispersive infrared analyzer with a desired bandpass filter utilizing an airtight cell filled with a preselected gas.

It is further object of the present invention to provide an non-dispersive infrared analyzer with increasing the utilizing portion of the infrared radiation emitted by the infrared source.

SUMMARY OF THE INVENTION

The foregoing objects are achieved and the foregoing deficiencies are overcome by the present invention.

The present invention has a single beam which is passed through a single cell; the beam passing through the cell can be referred to as a beam pass. A detector is provided which has selective sensitivity of the infrared radiation band corresponding to the absorption wavelength of a gas to be measured (hereinafter, the band is called s-band) and corresponding to the absorption wavelength of a preselected reference gas (hereinafter, the band is called r-band). Also, it employs two bandpass filters, one of which passes the s-band and the other passes the r-band. The two filters are inserted into the beam pass alternatively, so that infrared beam contained the different wavelength, i.e. the s-band and r-band, travels through the same beam pass and the same cell on a time sharing basis. Then, the infrared beam reaches the detector and alternatively provides two types of detector signals.

One of the detector signals is a signal which is proportional to the gas to be measured in the sample cell, which obtained at the time the s-band filter is inserted into the beam pass (hereinafter, the signal is called s-signal). The other detector signal is a signal which is an indicator of an overall performance of the beam system and the detector such as a fluctuation of the light source, detector sensitivity and/or stain of cell, which obtained at the time when the r-band filter is inserted into the beam pass (hereinafter, the signal is called r-signal). A normalized intensity ratio is calculated dividing the s-signal by r-signal. Then, the gas concentration is calculated from the normalized intensity ratio.

There are several selected combinations of two filters which can be utilized to perform the measurement. One of the most simple combinations is described above, and the other will be described in detail at the following section in this specification.

BRIEF DESCRIPTION OF THE DRAWINGS

The above and other objects and attendant advantages of the present invention will become readily apparent by reference to the following detailed description when considered in conjunction with the accompanying drawings, wherein.

DESCRIPTION OF THE PREFERRED EMBODIMENT (1) Embodiment 1-1

Figure 1:
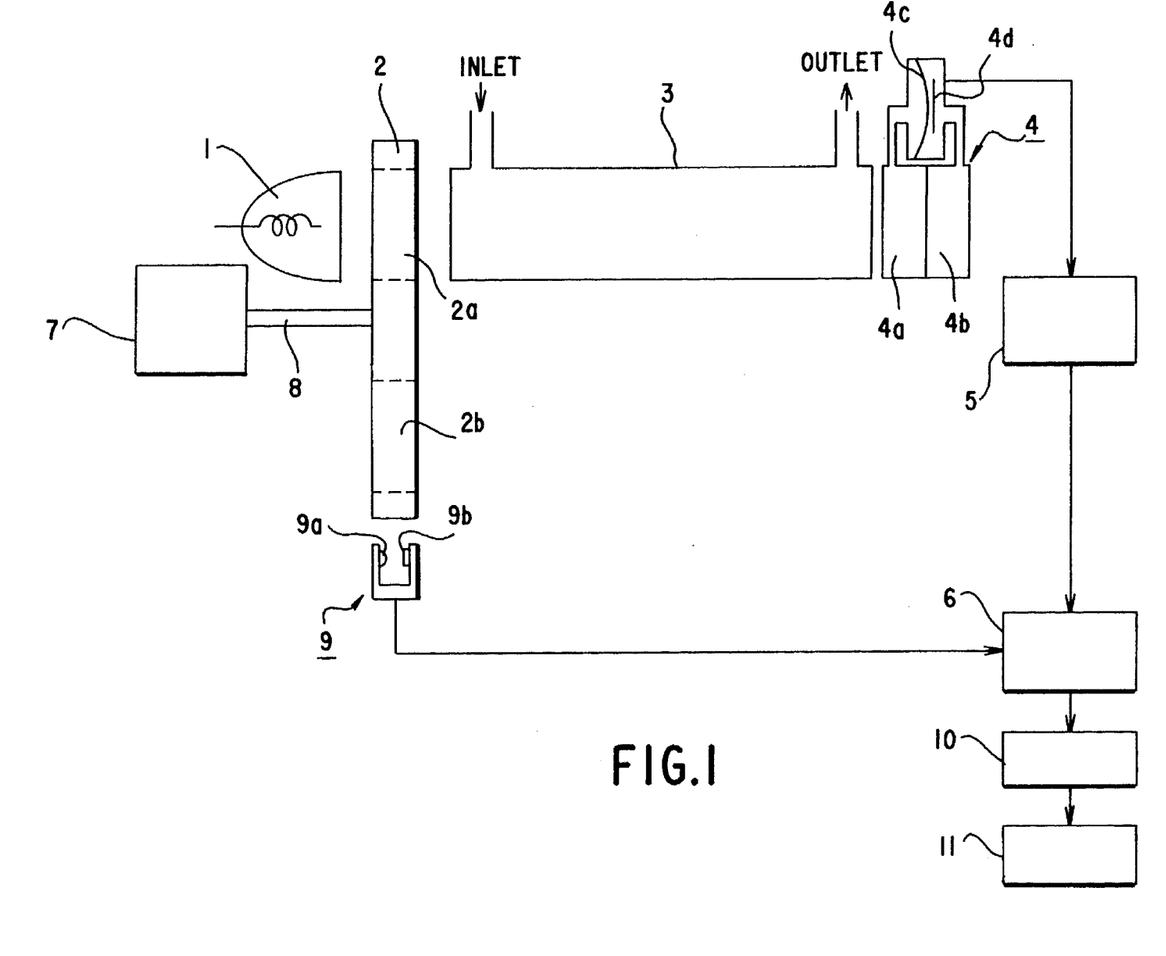
FIG. 1 illustrates one embodiment of a non-dispersive infrared analyzer constructed in accordance with the present invention.
Figure 2:
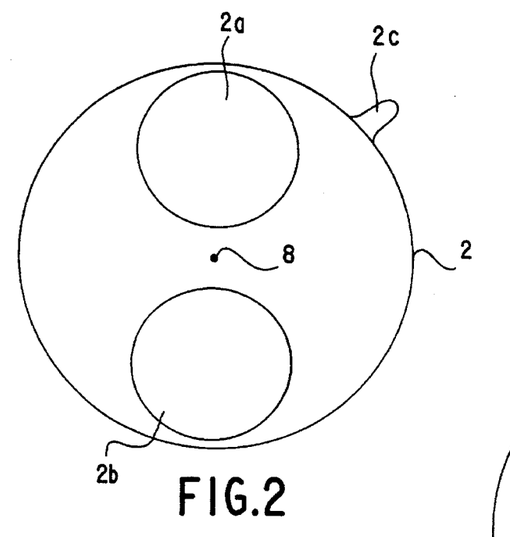
FIG. 2 depicts a rotating sector of the invention shown in FIG. 1.

FIG. 1 illustrates one embodiment of a non-dispersive infrared analyzer constructed in accordance with the present invention, and FIG. 2 depicts its rotating sector. The analyzer is designed, as an example, to measure carbon dioxide. In the FIG. 1 and FIG. 2, item 1 is an infrared source, item 2 is a rotating sector, items 2a and 2b are first and second filters, item 2c is a position marker, item 3 is a sample cell, and item 4 is a pneumatic detector. In detector 4, item 4a is a first chamber, item 4b is a second chamber, item 4c is a diaphragm, and item 4d is an electrode. Item 5 of the apparatus is an amplifier, item 6 is an electrical circuit, item 7 is a motor, item 8 is an axle, and item 9 is a position sensor. Finally, item 10 is a rectifier, and item 11 is a calculation device.

A sample gas stream containing the gas to be measured flows through sample cell 3. One of the pair of first and second filters 2a and 2b is second filter 2b which passes a narrow band of infrared radiation corresponding to a strong absorption band of the gas to be measured. First filter 2a passes a narrow band of infrared radiation which corresponds with a strong absorption band of the preselected reference gas. An essential character of the reference gas is that its absorption band does not overlap the absorption band of the gas to be measured. Hydrocarbons having few carbon atoms, such as methane, ethane and propane, can be used as a reference gas for measuring carbon dioxide, carbon monoxide, nitric oxide, and others. In this particular example, ethane is selected as the preselected reference gas.

The bandpass filters 2a and 2b may be of any type of commercially available filters. However, interference filters on sapphire substrates are preferred. In this case, first filter 2a passes an infrared radiation band of a bandwidth of 0.2 micrometers with a center point at 3.4 micrometers which corresponds with the absorption band of ethane. The second filter 2b passes an infrared radiation band of a bandwidth of 0.16 micrometers with a center point at 2.6 micrometers which corresponds with the absorption band of carbon dioxide.

Pneumatic detector 4 is basically the same structure and made of the same material as used in the prior art analyzer described above. However, chambers 4a and 4b are filled with the gas mixture of the same kind of gas as that to be measured and the same kind of gas as the preselected reference gas. In this case, a gas mixture of carbon dioxide and ethane, and argon which is a dilution gas, are charged in the chambers 4a and 4b. When infrared energy having the absorption band characteristic of the gas to be measured, or the absorption band characteristic of the preselected reference gas reaches to the detector, the gas mixture in the first chamber 4a absorbs the energy, and causes a capacitance change as discussed earlier between the diaphragm 4c and the electrode 4d.

Position sensor 9 is a photo sensor, which comprises light source 9a and light sensor 9b with a short distance therebetween. When the position marker 2c of rotating sector 2 comes to the space between the light source 9a and the light sensor 9b according to the rotation of the rotating sector 2, the position marker 2c interrupts the light being exposed to the sensor, so that the output signal of the light sensor 9b is changed.

In operation, the infrared beam emitted by the infrared source 1 is exposed to the cylindrical sample cell 3 through the filter 2a or 2b, which is inserted into the light beam periodically and alternatively by the rotation of the rotating sector 2.

The infrared light passed through the first or second filter 2a or 2b travels through the sample cell 3 and reaches pneumatic detector 4.

During the operation of the analyzer, rotating sector 2 rotates at a frequency of 1 Hz by means of the motion of the motor 7, which connected to the rotating sector 2 by the axle 8. First and second filters 2a or 2b are therefore inserted into the beam alternatively. The position sensor 9 detects the position marker 2c and feeds the position signal to the processor 6. The electrical circuit then determines which filter is inserted into the beam pass using the position signal.

Figure 7:
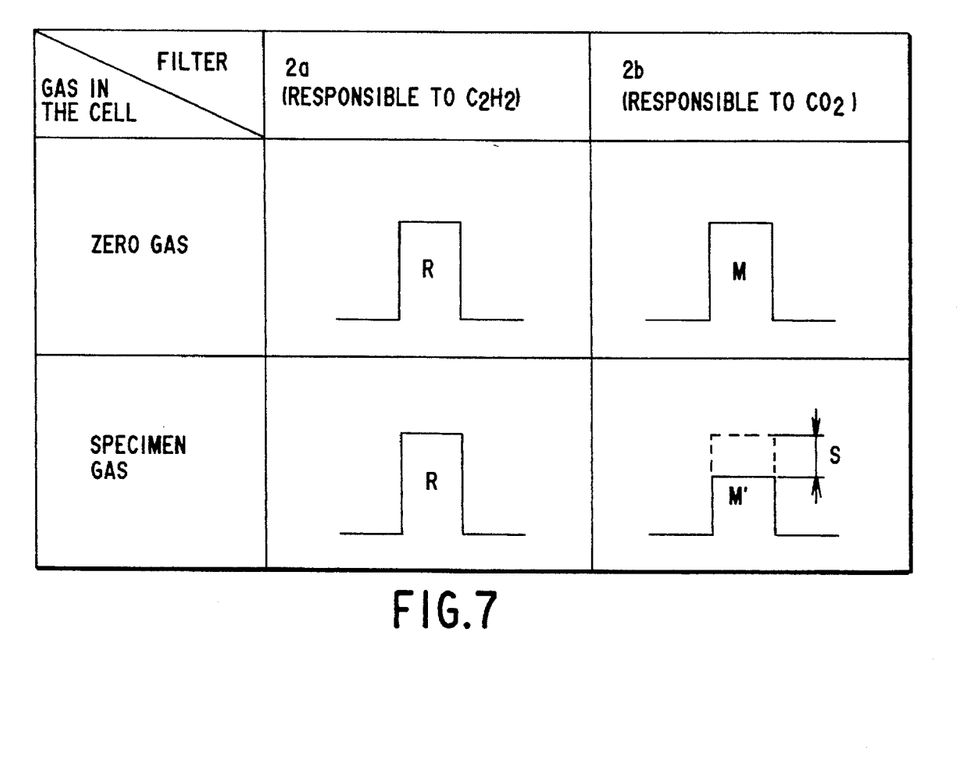
FIG. 7 is a table which illustrates the matrix of signal intensity of a detector according to the embodiment 1-1 on a condition of a given filter in a beam pass and a given gas filled in a sample cell.

Referring now to FIG. 7, the signal process will be described. FIG. 7 shows the matrix of the signal intensity of the detector according to the embodiment 1-1 on a condition of a given filter in the beam pass and a given gas filled in the sample cell.

A zero gas is a gas which does not include the gas to be measured, in this case carbon dioxide, nor include the preselected reference gas, in this case ethane. The first filter 2a passes a narrow band of infrared radiation which corresponds with a strong absorption band of the reference gas, and the second filter 2b passes a narrow band of infrared radiation which corresponds with a strong absorption band of the gas to be measured as described above.

In FIG. 7, the symbols M, M', R and S represent the signal intensity of the detector 4. On the matrix, the line indicates the filter in the beam pass and the row indicates the gas in a sample cell.

When the filter is 2a and the gas is a specimen gas, the infrared energy passed through the cell has an energy band which corresponds with the absorption band of the ethane gas. Because the specimen gas does not include ethane gas as the constituent gas, the infrared energy exposed to the cell does not diminish through the sample cell; as a result, the same energy reaches the detector. The ethane gas charged in the detector chamber 4a absorbs the energy, and the detector 4 gives the R-signal.

When the filter is 2a and the gas is a zero gas, the detector 4 gives the same R-signal. The R-signal is an indicator of an overall performance of the beam system.

On the other hand, when the filter is 2b and the gas is a specimen gas, the infrared energy passing through the cell has an energy band which corresponds with the absorption band of the carbon dioxide. Because the specimen gas includes carbon dioxide as the constituent gas, a certain part of the infrared energy which is proportional to the carbon dioxide concentration in the specimen gas is diminished by absorption, and the rest of the infrared energy reaches to the detector.

The carbon dioxide charged in the detector chamber 4a absorbs the residual energy, and the detector 4 provides an M'-signal.

The processor identifies the M'-signal and the R-signal using the position signal receiving from the position sensor 9.

The M'-signal and the R-signal are fed to rectifier 10 where the normalized intensity ratio M'/R is calculated by dividing the M'-signal by R-signal.

Next, the normalized intensity ratio is fed to calculation device 11. Calculation device 11 converts the ratio into the concentration of the carbon dioxide in the cell according to the predetermined relationship between the concentration and the M'/R ratio.

(2) Embodiment 1-2

Embodiment 1-2 of the non-dispersive infrared analyzer is essentially the same as the embodiment 1-1, except for the combination of first and second filters 2a and 2b, and signal processing at the processor 6. Embodiment 1-2 also measures a concentration of carbon dioxide in a specimen gas.

First filter 2a is a bandpass filter which passes a narrow band of infrared radiation which corresponds with a strong absorption band of the preselected reference gas, an essential character of which is that the absorption band of the reference gas does not overlap the absorption band of the gas to be measured. In this case, ethane is selected as the reference gas. The interference filter used is the same as filter 2a in embodiment 1-1.

Second filter 2b is a filter which is transparent for the infrared light emitted by the infrared source. In this case, filter 2a is an aperture on rotating sector 2.

Figure 8:
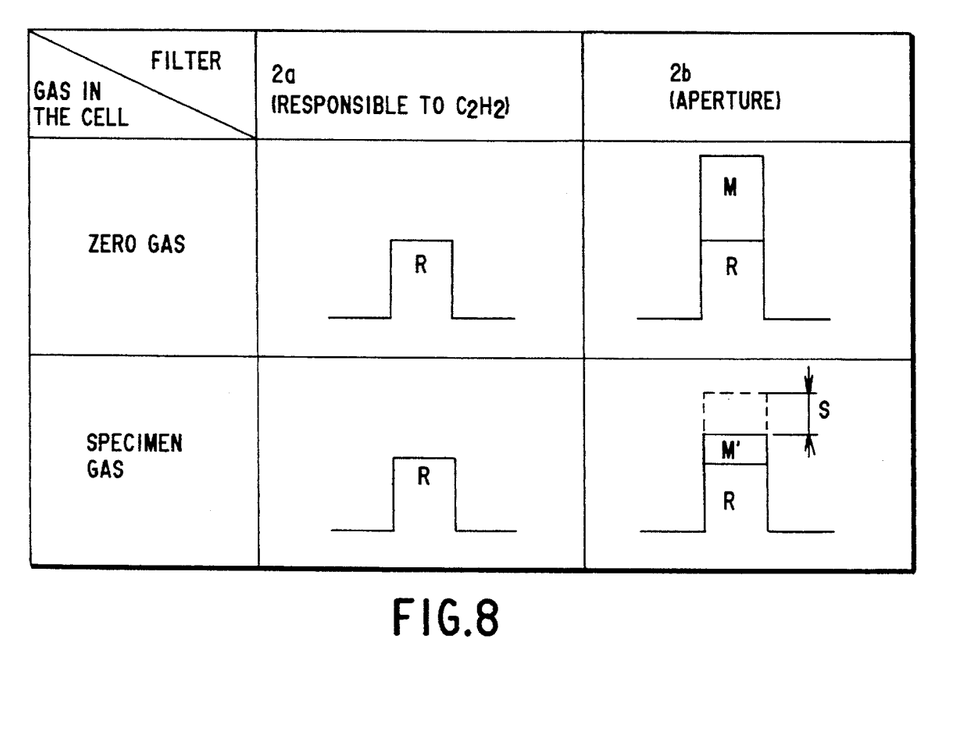
FIG. 8 is a table which illustrates the matrix of signal intensity of a detector according to the embodiment 1-2 on a condition of a given filter in a beam pass and a given gas filled in a sample cell.

Referring now to FIG. 8, the operation and the signal process will be described. FIG. 8 shows the matrix of the signal intensity of the detector according to the embodiment 1-2 on a condition of a given filter in the beam pass and a given gas filled in the sample cell.

When the filter is 2a, the detector gives the same R-signal, independent of the kind of gas in the cell, as in embodiment 1-1. When the filter is 2b, the infrared energy exposed to the cell has the whole spectra band energy, which includes the energy band corresponding with the absorption band of carbon dioxide and the energy band corresponding with the absorption band of ethane. When the gas charged in the cell is zero gas, the energy corresponding with carbon dioxide and with ethane does not diminish in the cell. All of the energy, including the two energy bands, reaches the detector. The carbon dioxide and the ethane charged in the detector chamber absorb the energy and provide the (R+M)-signal, where R is proportional to the energy corresponding with the absorption band of ethane and where M is proportional to the energy corresponding with the absorption band of carbon dioxide, both in the emitted light by the light source. Although the energy with the other band also reaches to the detector, the mixed gas in the chamber can not absorb the energy, so that the detector only generates the (R+M)-signal.

When the filter is 2b, and the gas is specimen gas, the part of the infrared energy exposed to the cell corresponds with the absorption band of carbon dioxide, and is absorbed by the constituent carbon dioxide gas in the cell. Thus, the detector gives (M'+R)-signal, which is S lower than the signal when the gas is zero gas.

Having the (M'+R)-signal and the R-signal, the processor can calculate the M'-signal by subtracting the R-signal from the (M'+R)-signal.

Then the rectifier and the calculator process the signal in the same manner described in the embodiment 1-1.

(3) Embodiment 1-3

The embodiment 1-3 of the non-dispersive infrared analyzer is similar to that shown in embodiment 1-1, except for the combination of the first and second filter 2a and 2b and signal processing at the processor 6. The embodiment 1-3 also is intended to measure a concentration of carbon dioxide in a specimen gas.

The first filter 2a is a bandpass filter which passes a narrow band of infrared radiation which corresponds with a strong absorption band of the carbon dioxide. The interference filter used is the same as the filter 2b in the embodiment 1-1. The second filter 2b is a filter which is transparent for the infrared light emitted by the infrared source. In this case the filter 2b is an aperture on the rotating sector 2, which is same as the filter 2b in the embodiment 1-2.

Figure 9:
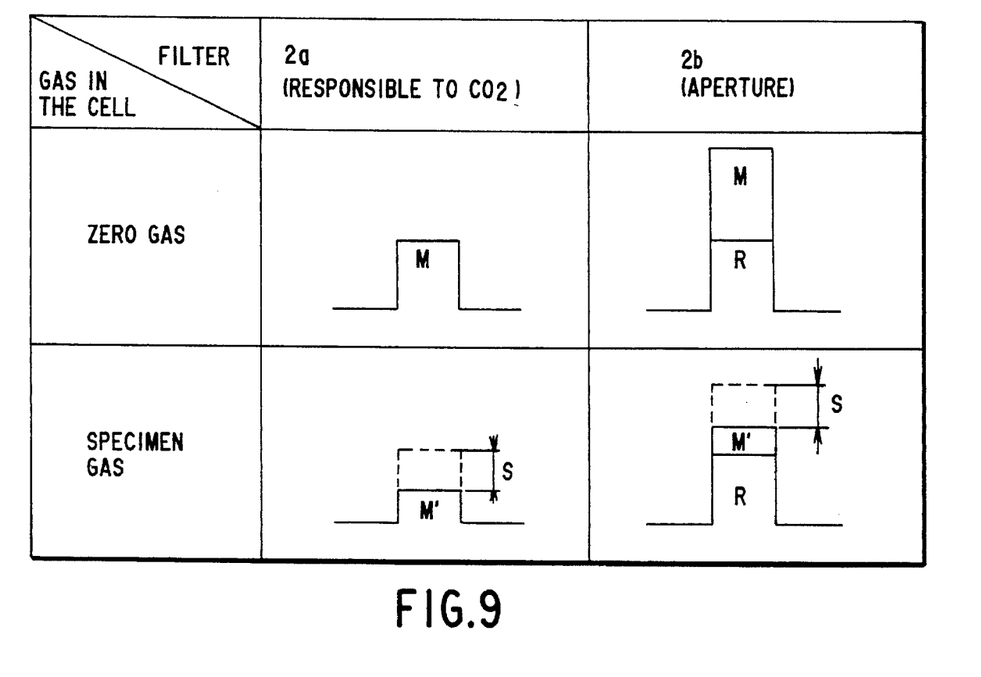
FIG. 9 is a table which illustrates the matrix of signal intensity of a detector according to the embodiment 1-3 on a condition of a given filter in the beam pass and a given gas filled in a sample cell.

Referring now to FIG. 9, the operation and signal process will be described. FIG. 9 shows the matrix of the signal intensity of the detector according to the embodiment 1-3 on a condition of a given filter in the beam pass and a given gas filled in the sample cell, similar to the tables shown in FIGS. 7 and 8.

When the filter is 2a and the gas is the specimen gas, the detector gives the M'-signal. When the filter is 2b and the gas is the specimen gas, the detector gives the (M'+R)-signal. The processor calculates the R-signal by subtracting the M'-signal from the (M'+R)-signal.

Then, the rectifier and the calculation device process the signal in the same way described in embodiment 1-1.

Embodiment 2-1

Figure 3:
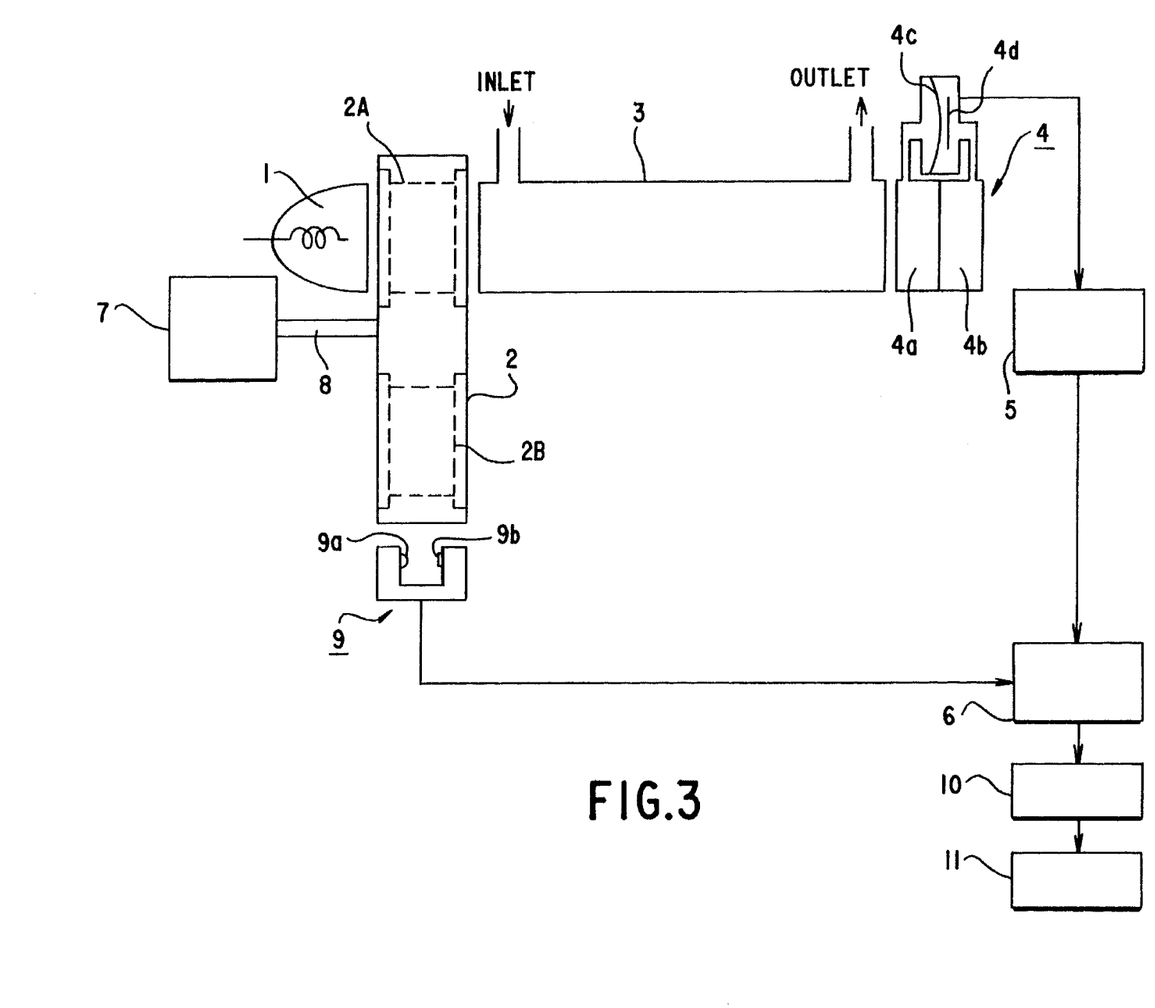
FIG. 3 illustrates another embodiment of non-dispersive infrared analyzer constructed in accordance with the invention.
Figure 4:
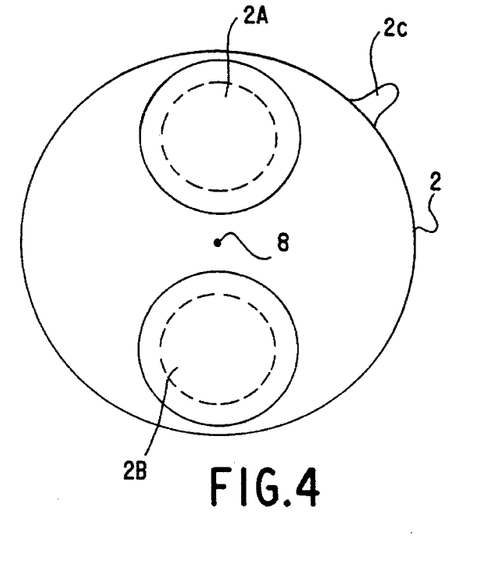
FIG. 4 depicts a rotating sector of the embodiment shown in FIG. 3;.

Embodiment 2-1 of the non-dispersive infrared analyzer is essentially same as the embodiment 1-1, except the first and second filter 2A and 2B are airtight cells. The analyzer of embodiment 2-1 is also intended to measure a concentration of carbon dioxide in the specimen gas.

FIG. 3 illustrates an analyzer constructed in accordance with embodiment 2-1, and FIG. 4 depicts its rotating sector. The components which are the same as the one of the embodiment 1-1 is indicated the same numerical number in the FIG. 1 and FIG. 2.

In the FIG. 3, 2A and 2B are filters, which are airtight cells placed on the rotating sector 2. The airtight cells can be of any shape. One of the example is a cylindrical shape, of which the cylindrical wall is made of aluminum. The both ends of each cylindrical airtight cell are equipped with cell windows through which infrared beam passes. The cell windows are made of plate of which material is transparent to infrared light such as calcium fluoride, $CaF_2$.

The first filter 2A is an airtight cell which is charged with the same kind of gas to be measured, in this case carbon dioxide. If the water vapor is the gas to be measured, ammonia gas which has the almost same character of infrared absorption can be used instead of the water as the charge gas in the airtight cell. The second filter 2B is an airtight cell which is charged with the same kind of preselected reference gas, an essential character of which is that its absorption band does not overlap the absorption band of the gas to be measured. In this case, the airtight cell 2B is charged with ethane.

Figure 10:
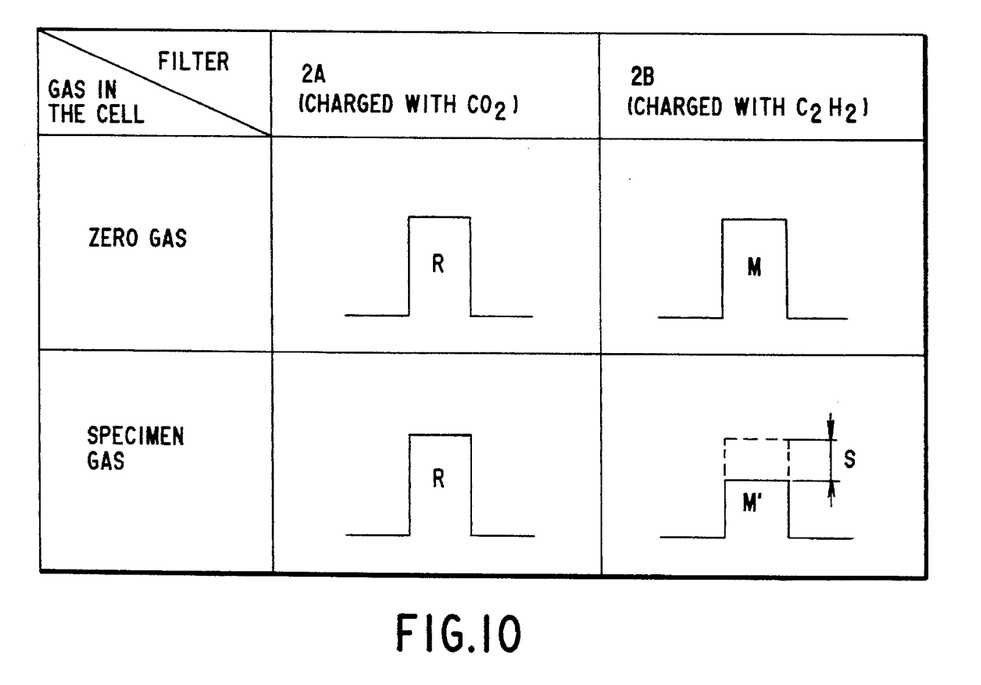
FIG. 10 is a table which illustrates the matrix of signal intensity of a detector according to the embodiment 2-1 on a condition of a given filter in a beam pass and a given gas filled in a sample cell.

Referring now to FIG. 10, the operation and the signal process will be described. FIG. 10 shows the matrix of the signal intensity of the detector according to the embodiment 2-1 on a condition of a given filter in the beam pass and a given gas filled in the sample cell, as the same as the FIG. 7.

The filter 2A passes the whole infrared energy except the energy corresponding with the absorption band of carbon dioxide due to the energy absorption by the carbon dioxide gas in the airtight cell. Similarly, the filter 2B passes the whole infrared energy except energy corresponding with the absorption band of ethane.

When the filter is 2A and the gas is a specimen gas, the infrared beam exposed to the cell has the whole energy band except the band corresponding with the absorption band of the carbon dioxide. Because the specimen gas does not include the ethane gas as the constituent gas, the infrared energy corresponding to the band of ethane exposed to the cell, does not diminish through the sample cell. The detector chamber is filled with carbon dioxide and ethane so that the energy having other than the energy band of carbon dioxide and ethane does not affect the output signal of the detector. Thus, the detector gives R-signal.

When the filter is 2b and the gas is a specimen gas, the infrared energy exposed to the cell has the whole energy except the band corresponding with the absorption band of the ethane. Because the specimen gas includes carbon dioxide, a part of the infrared energy having the band corresponding with the carbon dioxide exposed to the cell is diminished by absorption, a degree of which is proportional to the concentration of the carbon dioxide in the specimen gas. The rest of the infrared energy of the particular band as well as the energy of other band reaches the detector. Again, because the detector chamber does not contain gasses other than carbon dioxide and ethane, the energy having other band reaches to the detector does not affect the detector output. Thus, the detector gives M'-signal.

The following data process is the same as the one described in the previous embodiments.

(5) Embodiment 2-2

The embodiment 2-2 of the non-dispersive infrared analyzer is essentially the same as the embodiment 2-1, except the combination of the first and second filter 2A and 2B, and signal processing at the processor 6. The embodiment 2-2 is also intended to measure a concentration of carbon dioxide in a specimen gas.

The first filter 2A is an airtight cell charged with carbon dioxide. The second filter 2B is a filter which is transparent for the infrared light. The second filter 2B can be an airtight cell which is charged with the gas which does not absorb infrared light, such as nitrogen, or argon. Second filter 2B can also be an aperture on rotating sector 2. In this case, an aperture on the rotating sector is used.

Figure 11:
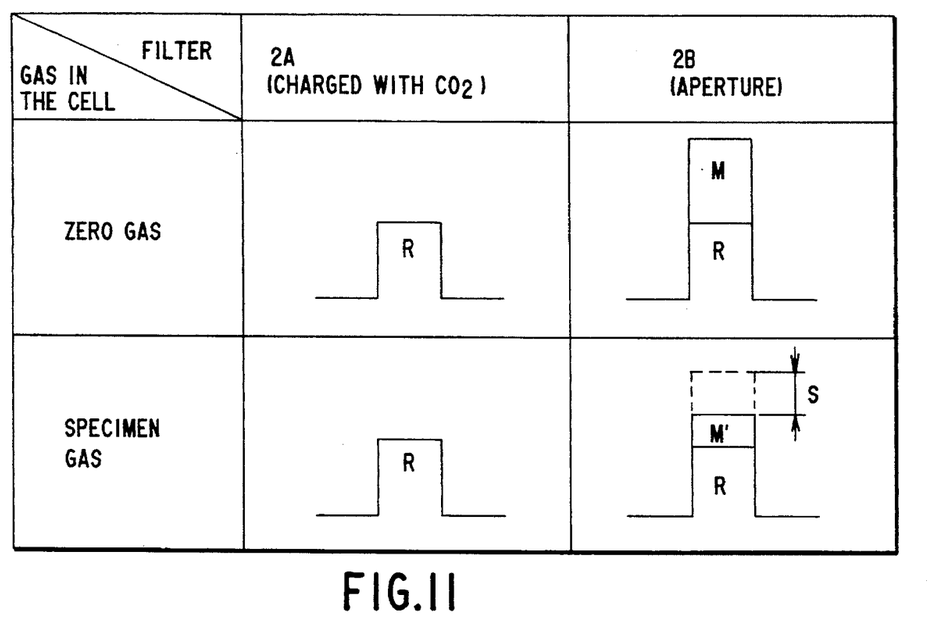
FIG. 11 is a table which illustrates the matrix of signal intensity of a detector according to the embodiment 2-2 on a condition of a given filter in a beam pass and a given gas filled in a sample cell.

Referring now to FIG. 11, the operation and the signal process will be described. FIG. 11 shows the matrix of the signal intensity of the detector according to the embodiment 2-2 on a condition of a given filter in the beam pass and a given gas filled in the sample cell, as the same as the FIG. 7.

When the filter is 2A and the gas is the specimen gas, the detector gives the R-signal. When the filter is 2B and the gas is the specimen gas, the detector gives the (M'+R)-signal. The processor calculates the M'-signal by subtracting the R-signal from the (M'+R)-signal.

Then the rectifier and the calculator process the signal with the same manner described in the previous embodiments.

(6) Embodiment 2-3

The embodiment 2-3 of the non-dispersive infrared analyzer is essentially the same as the embodiment 2-1, except the combination of the first and second filter 2A and 2B, and signal processing at the processor 6. The embodiment 2-3 also designs to measure a concentration of carbon dioxide in a specimen gas.

The first filter 2A is an airtight cell charged with ethane. The second filter 2B is a filter being transparent for the infrared light, in this case, an aperture on the rotating sector.

Figure 12:
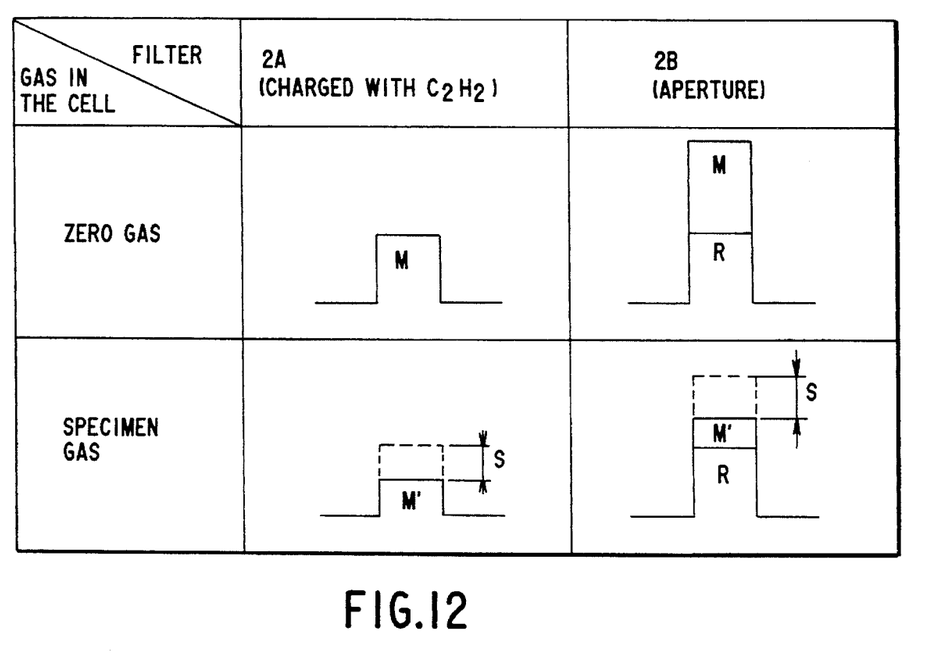
FIG. 12 is a table which illustrates the matrix of signal intensity of a detector according to the embodiment 2-3 on a condition of a given filter in a beam pass and a given gas filled in a sample cell.

Referring now to FIG. 12, the operation and the signal process will be described. FIG. 12 shows the matrix of the signal intensity of the detector according to embodiment 2-3 on a condition of a given filter in the beam pass and a given gas filled in the sample cell, the same as in FIG. 7.

When the filter is 2A and the gas is the specimen gas, the detector gives the M'-signal. When the filter is 2B and the gas is the specimen gas, the detector gives the (R+M')-signal. The processor calculates the R-signal by subtracting the M'-signal from the (M'+R)-signal.

Then the rectifier and the calculator process the signal with the same manner described in the previous embodiments.

The analyzer mentioned above in the six embodiments may be modified a number of ways, such as:

(1) When two preselected gases to be measured and reference gas of which absorption bands do not overlap are selected, and two bandpass filters responsible to the two gases and a filter responsible to the reference gas are placed on the rotating sector and the chambers of the pneumatic detector are filled with the gas mixture of the same kind of the two preselected gases and the reference gas, the apparatus can measure concentrations of the two preselected gases if the absorption bands of two preselected gases do not overlap;

(2) The rotating sector can be placed into the beam pass and between the sample cell and the pneumatic detector; and (3) The filters can be placed into the beam pass by a reciprocal movement of a sector plate having any shape.

In addition, it is readily apparent that the above-described invention has the advantage of wide commercially utility. It should be understood that the specific form of the invention hereinabove described is intended to be representative only, as certain modifications within the scope of these teachings will be apparent to those of ordinary skill in the art. Accordingly, reference should be made to the following claims, in determining the full scope of the invention.

What is claimed is:

1. A non-dispersive infrared analyzer, comprising:

an infrared light source which emits a beam of infrared light in a beam path;

a cell configured to have a gas flow therethrough, said cell having an infrared light passage through which a sample gas stream containing a gas to be measured and said infrared light beam emitted from said infrared source travels;

a sector disposed in said beam path, said sector having at least two means for filtering infrared light therein, said at least two means selected from the group consisting of a first means for filtering infrared light responsive to an absorption band of the gas to be measured, a second means for filtering infrared light responsive to an absorption band of a preselected reference gas which is not included in said sample gas, and a third means for filtering infrared light which is transparent to the infrared light beam emitted by the infrared source, said at least two means for filtering being alternatively inserted into the infrared beam, a detector in said beam path, said detector sensing a first wavelength of said infrared light beam which corresponds to the absorption band of the gas to be measured, and which senses an infrared band of a second wavelength corresponding to the absorption band of the preselected reference gas, and which receives the infrared light beam after said beam has traveled through the sample cell, said detector generating an electrical signal based upon detected infrared light, a position indicating means for detecting which of said first, second, and third means for filtering the infrared light is placed in the light path, and for generating a position signal corresponding thereto, processing means coupled to said detector and said position indicating means, for receiving the position signal from the position indicating means and receiving the electrical signal from the detector, said processing means producing a first signal representing a concentration of the gas to be measured in the cell, and producing a second signal representing overall sensitivity for infrared light of the infrared gas analyzer, rectifier means coupled to said processing means for receiving the first signal and the second signal from the processing means and producing a normalized intensity ratio thereof, calculating means coupled to said rectifier means for receiving the normalized intensity ratio and for calculating the concentration of the gas to be measured in the cell.

2. A non-dispersive infrared analyzer as recited in claim 1, wherein said detector comprises a pneumatic detector having a chamber therein, and wherein said chamber is filled with a combination of the gas to be measured and the preselected reference gas.

3. A non-dispersive infrared analyzer as recited in claim 1, wherein the first and second means for filtering infrared light comprise interference filters on a quartz substrate.

4. A non-dispersive infrared analyzer as recited in claim 1, wherein the first means for filtering infrared light comprises an airtight cell filled with the preselected reference gas.

5. A non-dispersive infrared analyzer as recited in claim 1, wherein the second means for filtering infrared light comprises an airtight cell filled with the gas to be measured.

6. A non-dispersive infrared analyzer as recited in claim 1, wherein said sector is a rotating sector connected to a rotating shaft, said sector being rotated such that said each of said at least two means for filtering are alternately inserted into the infrared beam by the rotation thereof.

7. A non-dispersive infrared analyzer as recited in claim 1, wherein said sector is disposed between said cell and said detector.

8. A non-dispersive infrared analyzer as recited in claim 1, wherein said sector is disposed between said infrared light source and said sample cell.

9. A non-dispersive infrared analyzer as recited in claim 1, wherein said sector comprises a sector plate having said at least two means for filtering thereupon, said sector plate being reciprocatibly movable within said beam path to alternatively insert said at least two means into the infrared beam.

10. A non-dispersive infrared analyzer as recited in claim 1, wherein said specimen gas to be measured and said reference gas are selected such that absorption bands thereof do not overlap.

11. A non-dispersive infrared analyzer as recited in claim 1, wherein said rectifier means produces a normalized intensity ratio by dividing the first signal by the second signal.

12. A non-dispersive infrared analyzer as recited in claim 1, wherein said preselected reference gas is a gas selected from a group of gases consisting of methane, ethane, and propane.

13. A non-dispersive infrared analyzer as recited in claim 1, wherein said gas to be measured is one gas of a group of gases consisting of carbon dioxide, carbon monoxide, and nitric oxide.

14. A method for determining a gas concentration, comprising the steps of:

providing a cell configured to have a gas flow therethrough, said cell having an infrared light passage through which a sample gas stream containing a gas to be measured, and an infrared light beam, travels;

flowing the sample gas stream through the cell;

irradiating an infrared light beam through said cell, whereby said infrared light beam and said sample gas stream share a common path;

alternatingly disposing at least two means for filtering infrared light in said beam path, said at least two means for filtering being selected from the group consisting of a first means for filtering infrared light responsive to an absorption band of the gas to be measured, a second means for filtering infrared light responsive to an absorption band of a preselected reference gas which is not included in the sample gas, and a third means for filtering infrared light which is transparent to the infrared light beam emitted by the infrared source;

sensing a first wavelength of the infrared light beam which corresponds to the absorption band of the gas to be measured;

sensing an infrared band of a second wavelength corresponding to the absorption band of the preselected reference gas, said sensing steps being carried out with a detector disposed in said beam path, said detector receiving the infrared light beam after the beam has traveled through the sample cell, said detector generating an electrical position signal based upon detected infrared light;

detecting which of the first, second, and third means for filtering the infrared light is being placed in the light path;

producing a first signal representing a concentration of the gas to be measured in the cell based upon the detected filter means and the generated electrical signal;

producing a second signal representing overall sensitivity for infrared light;

normalizing an intensity ratio of the first and second signals;

calculating the concentration of the gas to be measured based upon the normalized intensity ratio.

* * * * *